US006211123B1

(12) United States Patent
Brown et al.

(10) Patent No.: US 6,211,123 B1
(45) Date of Patent: Apr. 3, 2001

(54) LUBRICATING OIL COMPOSITIONS

(75) Inventors: Alisdair J. Brown, Oxfordshire; Ian A. W. Bell, Oxon; John A. Cleverley, Oxfordshire; Jose M. G. Gomes, Oxford, all of (GB); Edward I. Stiefel, Bridgewater; Jonathan M. McConnachie, Flemington, both of NJ (US)

(73) Assignee: Infineum USA L.P., Linden, NJ (US)

( * ) Notice: Subject to any disclaimer, the term of this patent is extended or adjusted under 35 U.S.C. 154(b) by 0 days.

(21) Appl. No.: 09/335,328

(22) Filed: Jun. 17, 1999

(30) Foreign Application Priority Data

Jun. 17, 1998 (GB) .................................................. 9813071

(51) Int. Cl.⁷ ..................... C10M 135/18; C10M 135/00
(52) U.S. Cl. ........................... 508/363; 508/368; 508/383
(58) Field of Search ............................................... 508/363

(56) References Cited

U.S. PATENT DOCUMENTS

| | | | |
|---|---|---|---|
| 2,951,040 | 8/1960 | Hugel et al. | 252/33.6 |
| 3,419,589 | 12/1968 | Larson et al. | 260/429 |
| 3,840,463 * | 10/1974 | Froeschmann et al. | 508/363 |
| 4,529,526 * | 7/1985 | Inoue et al. | 508/363 |
| 4,846,983 * | 7/1989 | Ward, Jr. | 508/363 |
| 4,849,123 * | 7/1989 | Tipton et al. | 508/363 |
| 4,966,719 | 10/1990 | Coyle et al. | 252/42.7 |
| 4,978,464 | 12/1990 | Coyle et al. | 252/42.7 |
| 4,995,996 | 2/1991 | Coyle et al. | 252/42.7 |
| 5,308,519 * | 5/1994 | Spiess et al. | 508/363 |
| 5,726,131 | 3/1998 | Froeschmann | 508/271 |
| 5,824,627 * | 10/1998 | McConnachie et al. | 508/363 |
| 5,888,945 * | 3/1999 | Stiefel et al. | 508/363 |
| 5,906,968 * | 5/1999 | McConnachie et al. | 508/363 |

FOREIGN PATENT DOCUMENTS

| | | |
|---|---|---|
| 0 286 140 | 10/1988 | (EP) . |
| 0 534 357 | 3/1993 | (EP) . |
| WO 98/26030 | 6/1998 | (WO) . |

OTHER PUBLICATIONS

Chemical Abstract 218401g, vol. 124, No. 16, Apr. 15, 1996 Wu et al., "Synthesis, Structures and Reactivity of Incomplete Cubane–like Compound" (XP–002118549).
Chemical Abstract 150114s, vol. 122, No. 12, Mar. 20, 1995 Fedin et al., "Demonstration of the Substitution of Selenium for Sulfur in Selenium Cluster Complexes of Niobium and Tungsten and Characteristics of Mixed Sulfur–Selenium Complexes by the FAB mass Spectrometry Method" (XP–002118548).
Chemical Abstract 138435g, vol. 118, No. 14, Apr. 5, 1993 Shibahara et al., "Synthesis of Sulfur–Bridged Molybdenum and Tungsten Coordination Compounds" (XP–002118550).
"Identification and Characterization of Trinuclear Molybdenum–Sulfur Clusters by Fast Atom Bombardment (FAB) Mass Spectrometry", Inorganic Chemistry, vol. 30, No. 4, Feb. 20, 1991, pp. 873–876 (XP–002102746).

* cited by examiner

Primary Examiner—Ellen M. McAvoy

(57) ABSTRACT

A lubricating oil composition is provided comprising a major amount of an oil of lubricating viscosity and a minor amount of, as an additive, at least one compound comprising a trinuclear tungsten core and bonded thereto a ligand or ligands capable of rendering the compound oil-soluble or oil-dispersible.

24 Claims, No Drawings

LUBRICATING OIL COMPOSITIONS

FIELD OF THE INVENTION

The present invention relates to lubricating oil compositions and concentrates therefor containing tungsten compounds and methods of making them.

BACKGROUND OF THE INVENTION

Molybdenum sulfur-containing compounds have been proposed and investigated as lubricant additives. U.S. Pat. Nos. 2,951,040; 3,419,589; 3,840,463; 4,966,719; 4,995,996; and 4,978,464 are representative of patent specifications describing both molybdenum and sulfur.

Molybdenum compounds for use as lubricant additives described in the art are principally dinuclear molybdenum compounds, characterised by the oxidation state Mo(V). However, International Patent Application No. PCT/IB97/01656 describes use of trinuclear molybdenum compounds as lubricant additives, i.e. characterised by a different oxidation state (Mo(IV); trinuclear molybdenum compounds have improved properties as lubricating additives compared with dinuclear molybdenum compounds as evidenced by test results in the above International Patent application, thus ameliorating the problem of providing improved lubricant performance in response to demands from original equipment manufacturers (OEM's).

The present invention provides tungsten analogues of the aforementioned trinuclear molybdenum compounds that are useful as additives in lubricating oil compositions.

SUMMARY OF THE INVENTION

In a first aspect, the invention is a lubricating oil composition comprising, or made by mixing, a major amount of an oil of lubricating viscosity and a minor amount of, as an additive, at least one compound comprising a trinuclear tungsten core and bonded thereto a ligand or ligands capable of rendering the compound oil-soluble or oil-dispersible. Preferably, the core, e.g. as a cluster, contains non-metallic atoms consisting wholly or partly of sulfur and more preferably it consists of trinuclear tungsten and sulfur. The additive may be in the form of mixtures of such compounds.

The compound may provide at least 1, for example 1 to 2,000, such as 5 to 1,000, preferably 20 to 1,000, ppm by mass of the tungsten, expressed as tungsten atoms, based on the mass of the composition.

The lubricating oil compositions according to the first aspect of the invention may have excellent antiwear, antioxidant, and friction-reducing properties; also they may be compatible with other additives used in formulating commercial lubricating oil compositions and can be made from readily available starting materials.

In a second aspect, the invention is an additive concentrate for blending with an oil of lubricating viscosity comprising, or made by mixing, an oleaginous carrier and from 1 to 200,000, for example 50 to 150,00 such as 50 to 100,000, ppm by mass of the tungsten, expressed as tungsten atoms, of an additive defined in the first aspect of the invention, based on the mass of the concentrate.

In a third aspect, the invention is a compound having the formula $W_3S_kL_nQ_z$ wherein L represents a ligand or independently selected ligands, n is from 1 to 4, k is at least 4, for example from 4 to 10, such as 4 to 7, Q is a neutral electron donating compound, and z ranges from 0 to 5, wherein the compound has a core having the structure

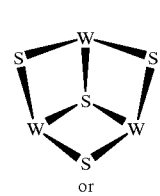

or

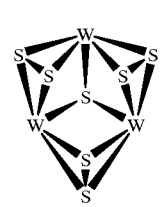

In a fourth aspect, the invention is a method of lubricating an internal combustion engine comprising operating the engine and lubricating the engine with a lubricating oil composition of the first aspect of the invention.

In a fifth aspect, the invention is use of an additive as defined in the first aspect of the invention for enhancing one or more lubricating oil properties of a lubricating oil composition.

In a sixth aspect, the invention is a method for preparing a compound comprising a trinuclear thiotungsten core and bonded thereto a ligand or ligands capable of rendering the compound oil-soluble or oil-dispersible, which method comprises reacting a trinuclear thiotungsten source and a source of said ligand or ligands, to form said compound. The thiotungsten source may, for example, be a compound containing the $[W_3S_4$ or $_7X_6]^{2-}$ ion where X represents halogen such as chlorine or bromine.

In a seventh aspect, the invention is a method of preparing a lubricating oil composition or an additive concentrate comprising mixing an additive defined in the first aspect of the invention with an oil of lubricating viscosity or an oleaginous carrier.

In particular, use, at least partly, may be made of the processes described by V. P. Fedin et al in Polyhedron, II, (24), 3159 (1992) and in Inorg. Chim. Acta, 18781 (1991). For example, the compound containing the $[W_3S_7X_6]^{2-}$ ion, where the cation may be a quaternary ammonium ion, may be reacted with an alkali metal compound of the ligand. Such ion-containing compound may be made from the compound $W_3S_7X_4$ by reacting it with a quaternary ammonium halide/hydrogen halide mixture. Alternatively, the trinuclear tungsten compounds may be made directly from the compound $W_3S_7X_4$ by reacting with a phosphonium halide and then an alkali metal compound of the ligand.

The compound $W_3S_7X_4$ may be made by reacting tungsten, sulphur and a halogen, or by reacting a tungsten sulphide (e.g. $WS_3$) and a phosphorus halide, both under conditions of high temperature, Furthermore, use may be made of the process described by Shibahara T et al in Inorg. Chem. 1992, 31, 640–647 which, in particular, describes making the trinuclear tungsten aquo complex cation, $[W_3S_4(H_2O)_9]^{4+}$. Most members of the series, $[W_3O_xS_{4-x}(H_2O)_9]^{4+}$ where x is from 0 to 4, may be similarly synthesised. The ligands of the invention, e.g. dithiocarbamate ("dtc"), are combined with these cations, eg by reacting with dithiocarbamic acid (e.g. 4.4 moles) in the presence of sodium hydroxide to form compounds used in the invention.

Additionally, use may be made of the process described by Shibahara T et al in Inorg. Chem. 1994, 33, 292–301 to prepare compounds comprising a mixed metal trinuclear molybdenum/tungsten core, which compounds are within the scope of the present invention. Thus, there is described making the aquo complex cations, $[MoW_2S_4(H_2O)_9]^{4+}$ and $[Mo_2WS_4(H_2O)_9]^{4+}$, which are combined with the ligands of the present invention, eg "dtc", by reacting with dithiocarbamic acid (eg 4.4 moles) to form compounds useful in the present invention.

In this specification:

"comprising" or any cognate word is taken to specify the presence of stated features, integers, steps or components, but does not preclude the presence or addition of one or more other features, integers, steps, components or groups thereof;

"major amount" means in excess of 50 mass % of the composition;

"minor amount" means less than 50 mass % of the composition, both in respect of the stated additive and in respect of the total mass % of all of the additives present in the composition, reckoned as active ingredient of the additive or additives;

the invention also provides the product obtained or obtainable as a result of any reaction between the various additive components of the composition or concentrates, essential as well as customary and optimal, under the conditions of formulation, storage or use;

"oil-soluble" or "dispersible" used herein do not necessarily indicate that the compounds or additives are soluble, dissolvable, miscible, or capable of being suspended in the oil in all proportions. These do mean, however, that they are, for instance, soluble or stably dispersible in oil to an extent sufficient to exert their intended effect in the environment in which the oil is employed. Moreover, the additional incorporation of other additives may also permit incorporation of higher levels of a particular additive, if desired.

DETAILED DESCRIPTION OF THE INVENTION

Oil of Lubricating Composition

This oil may be selected from vegetable, animal, mineral, or synthetic oils. The oils may range in viscosity from light distillate mineral oils to heavy lubricating oils such as gas engine oil, mineral lubricating oil, motor vehicle oil, and heavy duty diesel oil. The oils may be unrefined, refined, and re-refined. The oil may be used oil.

In general, the viscosity of the oil will range from 2 to 30, especially in the range of 5 to 20, $mm^2 \, s^{-1}$ at 100° C. The oil may, for example, be free of sulfur.

Compounds

The compounds may, for example, have the formula formula $W_3S_kL_n$ or mixtures thereof, wherein L represents a ligand which is independent from other ligands represented by L when n is more than 1;

n is in the range from 1 to 4; and k is at least 4, for example in the range from 4 to 10, such as 4 to 7, preferably 4 or 7.

Also, the compounds may have the formula $W_3S_kE_xL_n$ or mixtures thereof, wherein L and n are defined as above, k is at least 1, E is oxygen or selenium, x is at least 1, and the sum of k and x is at least 4.

The above formulae ($W_3S_kL_n$ and $W_3S_kE_xL_n$) may each additionally include a moiety $Q_z$ wherein Q represents a neutral electron-donating compound such as water, amines, alcohols, phosphines and ethers, and z is in the range from 0 to 5 and includes non-stoichiometric values.

The $W_3S_k$ cores in the above formulae have a net charge of +4. Consequently, in order to neutralize such cores, the total charge among all ligands, L, in $W_3S_kL_n$, must be −4. Four monoanionic ligands, L, are preferred. As indicated in the formulae, it is believed that oxygen and/or selenium may be substituted for sulfur in the core. However, in addition to the trinuclear tungsten, the core may contain non-tungsten hetero-atoms; these hetero-atoms should include at least one sulfur atom, and preferably be primarily (i.e., greater than 50%) sulfur. Most preferred is a core consisting of tungsten and sulfur alone. The balance, if any, is oxygen and/or selenium.

When the core consists only of trinuclear tungsten and sulfur it is represented by the formula $W_3S_k$, and with ligands attached is represented by the formula $W_3S_kL_n$.

The electron-donating compound, $Q_z$, is merely present in the preceding formulae to fill any vacant coordination sites on the trinuclear tungsten compound.

The ligand or ligands, including L, may be represented by the following formulae:

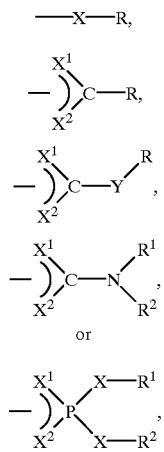

and mixtures thereof, and perthio derivatives thereof, wherein X, $X^1$, $X^2$ and Y are independently selected from the group of oxygen and sulfur, and wherein $R^1$, $R^2$, and R are independently selected from the group consisting of H and organo groups that may be the same or different. Preferably the organo groups are hydrocarbyl groups such as alkyl (e.g., in which the carbon atom attached to the remainder of the ligand is primary, secondary or tertiary), aryl, substituted aryl and ether groups. More preferably, all ligands are the same.

Importantly, the organo groups of the ligands have a sufficient number of carbon atoms to render the compounds soluble or dispersible in the oil. The compounds' oil solubility or dispersibility may be influenced by the number of carbon atoms in the ligands. Preferably the ligand source chosen has a sufficient number of carbon atoms to render the compound soluble or dispersible in the oil. In the compounds in the present invention, the total number of carbon atoms present among all of the organo groups of the compounds' ligands typically will be at least 21, e.g. 21 to 800, such as at least 25, at least 30 or at least 35. For example, the number of carbon atoms in each alkyl group will generally range between 1 to 100, preferably 1 to 40 and more preferably between 3 and 20. Preferred ligands include dialkyldithiophosphate ("ddp"), xanthates, thioxanthates, dialkylphosphate, dialkyldithiocarbamate ("dtc"), and carboxylate; of these dtc is more preferred.

Multidentate organic ligands containing at least two of the above functionalities are also capable of binding to at least one of the trinuclear cores and serving as ligands. Without wishing to be bound by any theory, it is believed that one or more trinuclear tungsten cores may be bound or interconnected by means of at least one of these multidentate ligands. Such structures fall within the scope of this invention. This includes the case of a multidentate ligand having multiple connections to one core.

Those skilled in the art will realise that formation of the compounds will require selection of appropriate ligands having suitable charge to balance the corresponding core's charge, The term "hydrocarbyl" denotes a substituent having carbon atoms directly attached to the remainder of the ligand and which is predominantly hydrocarbyl in character within the context of this invention. Such substituents include the following: (1) hydrocarbon substituents, that is, aliphatic (for example alkyl or alkenyl), alicyclic (for example cycloalkyl or cycloalkenyl) substituents, aromatic-, aliphatic- and alicyclic-substituted aromatic nuclei, as well as cyclic substituents wherein the ring is completed through another portion of the ligand (that is, any two indicated substituents may together form an alicyclic group); (2) substituted hydrocarbon substituents, that is, those containing nonhydrocarbon groups which, in the context of this invention, do not alter the predominantly hydrocarbyl character of the substituent. Those skilled in the art will be aware of suitable groups (e.g., halo, (especially chloro and fluoro), amino, alkoxyl, mercapto, alkylmercapto, nitro, nitroso, sulfoxy, etc.); (3) hetero substituents, that is, substituents which, while predominantly hydrocarbon in character within the context of this invention, contain atoms other than carbon present in a chain or ring otherwise composed of carbon atoms.

Compounds having the formula $W_3S_kL_nQ_z$ have cationic cores surrounded by anionic ligands that may be represented by structures (I) and (II) as depicted above.

In general, the trinuclear tungsten compounds can be purified by well known techniques such as chromatography; however, it may not be necessary to purify the compounds.

The lubricating oil compositions of the present invention may be prepared by adding to an oil of lubricating viscosity an effective minor amount of at least one trinuclear tungsten compound, which may be prepared in amounts as described previously, and, if necessary, one or more co-additives such as described hereinafter. This preparation may be accomplished by adding the trinuclear tungsten compound directly to the oil or by first mixing the trinuclear tungsten compound in a suitable carrier fluid to achieve oil-solubility or -dispersibility, and adding the mixture to the lubricating oil. Co-additives may be added to the oil by any method known to those skilled in the art, either prior to, contemporaneously with, or subsequent to addition of the trinuclear tungsten compound.

Concentrates of the trinuclear tungsten compounds and co-additives, if required, in a suitable oleagenous, typically hydrocarbon, carrier fluid provide a convenient means of handling them before their use. Oils of lubricating viscosity, such as those described above as well as aliphatic, naphthenic, and aromatic hydrocarbons are examples of suitable carriers for concentrates. These concentrates may contain 1 to 90 mass % of the additives based on the mass of the concentrate; preferred is 1 to 50, more preferably 20 to 50, mass %.

The lubricating oil compositions of the invention may be used to lubricate mechanical engine components, particularly of an internal combustion engine such as a spark-ignited or compression-ignited engine, by adding the compositions thereto as crankcase lubricants.

The trinuclear tungsten compounds of the present invention may also possess antioxidant properties when used in a lubricating oil composition.

Co-Additives

Other lubricant additives may be used for blending in the lubricating oil compositions of this invention. These include dispersants, detergents, e.g., single or mixed metal detergent systems, pour point depressants, viscosity improvers, antioxidants, surfactants, antiwear agents, and friction reducing agents. These can be combined in proportions known in the art. For example, additives containing phosphorus and/or sulfur compounds such as a zinc dialkyl dithiophosphate(ZDDP) can be prepared and used with the compounds of the present invention. However, the compounds of the present invention may be effective or may even possess improved properties when used in lubricating oil compositions that are free or substantially free of added phosphorus and/or sulfur. i.e., phosphorus and/or sulfur in addition to (i.e., except for) the phosphorus or sulfur contained in the trinuclear tungsten compounds themselves. A lubricating oil composition that is substantially free of phosphorus and/or sulfur is one in which the amount of phosphorus and/or sulfur is not more than is inherently present in base oils of lubricating viscosity.

Particularly noteworthy is the use of anti-oxidants in combination with the trinuclear tungsten compounds.

Examples of suitable antioxidants are selected from copper-containing antioxidants, sulfur-containing antioxidants, aromatic amine-containing antioxidants and phenolic antioxidants.

Examples of suitable copper-containing antioxidants include oil-soluble copper compounds described in EP-B-24 146, EP-A-280 579 and EP-A-280 580. Thus, for example, the copper may be blended into the oil as an oil-soluble copper salt of a synthetic or natural carboxylic acid. Examples of carboxylic acids from which suitable copper salts may be derived include $C_2$ to $C_8$ carboxylic acids (e.g., acetic acid, and fatty acids such as stearic acid and palmitic acid), unsaturated acids (e.g., oleic acid), branched carboxylic acids (e.g., naphthenic acids of molecular weight of from 200 to 500, neodecanoic acid and 2-ethylhexanoic acid), and alkyl- or alkenyl-substituted dicarboxylic acids (e.g., polyalkenyl-substituted succinic acids such as octadecenyl succinic acids, dodecenyl succinic acids and polyisobutenyl succinic acids). In some cases, suitable compounds may be derived from an acid anhydride, for example, from a substituted succinic anhydride. The copper antioxidant may be, for example, a copper dithiocarbamate or copper dithiophosphate. Other copper- and sulfur-containing antioxidant compounds, for example, copper mercaptides, xanthates, and thioxanthates, are also suitable for use in accordance with the invention, as are copper sulfonates, phenates (optionally sulfurized) and acetylacetonates. Other copper compounds which may be used in accordance with the invention are overbased copper compounds. Examples of such compounds, and of processes for their preparation, are described in U.S. Pat. No. 4,664,822 and EP-A-0 425 367. The copper compound may be in cuprous or cupric form.

Examples of suitable aromatic amine-containing antioxidants are aromatic amines which have at least one aromatic group directly attached to at least one amine nitrogen atom. Secondary aromatic amines, especially those having two aromatic groups attached to the same amine nitrogen atom, are preferred, but the use of other aromatic amines is not excluded. The amines may contain one or more aromatic groups, for example at least two aromatic groups. Where there are two aromatic groups, both are preferably bonded directly to the same amine nitrogen. Compounds in which two aromatic groups are linked by a covalent bond or by an atom or group (e.g., an oxygen or sulfur atom, or a —CO—, —SO$_2$— or alkylene group) may be used. Aromatic rings, which are preferably aromatic hydrocarbon rings, may be unsubstituted or substituted by one or more substituents selected from alkyl, cycloalkyl, alkoxy, aryloxy, acyl, acylamino, hydroxy, and nitro groups. Amines containing alkyl-substituted aromatic hydrocarbon rings are preferred, especially those containing two alkylsubstituted phenyl groups. Preferred N-aryl amines for use in accordance with the invention are naphthylamines and, especially, diphenylamines, including alkyl substituted diphenylamines, wherein the alkyl group may be the same or different, having 1 to 28 carbon atoms. Other nitrogen-containing antioxidants, for example, phenothiazine type compounds, may also be used in this invention.

Examples of phenolic antioxidants include (a) sterically hindered tertiary-alkylated monohydric phenols such as those described in more detail in U.S. Pat. Nos. 2,944,086; 3,043,775; and 3,211,652; and (b) methylene-bridged tertiary alkyl polyphenols, such as 4,4'-methylene bis (2,6-di-tertbutylphenol) and 2,2'-methylene bis (4,6-di-(1,1,2-trimethylpropyl)phenol), and mixtures of (a) and (b) such as those described in more detail in EP-B-0456925.

Examples of sulfur-containing antioxidants (compounds) are alkaline earth metal salts of alkylphenolthioesters having preferably C$_5$ to C$_{12}$ alkyl side chains, calcium nonylphenol sulfide, ashless oil-soluble phenates and sulfurized phenates, phosphosulfurized or sulfurized hydrocarbons, phosphorus esters and other sulfur-and molybdenum-containing compounds. Other examples of sulfur-containing antioxidants are metal salts of dihydrocarbyl dithiophosphate or dihydrocarbyl dithiocarbamate compounds, wherein the metal is selected from Zn, Mn, Ni, Al, Group 1 metals and Group 2 metals. Other sulfur-containing compounds include those described in EP-A-699 759, for example, sulfides of oils, fats or polyolefins, in which a sulfur group having two or more sulfur atoms is adjoined and bonded together in a molecular structure. Examples include sulfurized sperm oil, sulfurized pinene oil, sulfurized soybean oil, sulfurized polyolefin, sulfurized esters, dialkyl disulfide, dialkyl polysulfide, dibenzyl disulfide, ditertiary butyl disulfide, polyolefin polysulfide, a thiadiazole type compound such as bis-alkyl polysulfide thiadiazole, and sulfurized phenol.

Preferable antioxidants are copper-containing antioxidants, aromatic amine-containing compounds including diphenylamines and derivatives thereof that have an effect herein comparable to diphenylamines), and mixtures thereof. Examples of copper containing antioxidants include copper polyisobutylene succinic anhydride ("copper PIBSA") and copper oleate; diphenylamines include all effective derivatives of diphenylamines.

Thus, the lubricating oil compositions of the present invention may include a minor amount of at least one antioxidant and at least one oil-soluble or oil-dispersible trinuclear tungsten compound. The composition may include a mixture of the trinuclear tungsten compounds and antioxidants of the types disclosed herein, the lubricating oil and/or other additives disclosed herein per se, and/or of any intermediates and reaction products occurring as a result of the mixture. In combination, the antioxidants and trinuclear tungsten compounds are present in a minor effective amount to produce the enhanced lubricating performance, particularly friction reduction, friction reduction retention, antioxidancy and/or antiwear properties in the oil.

EXAMPLES

The invention will now be particularly described, by way of example only, as follows.

Example 1

Preparation of $W_3S_7Br_4$

Tungsten (5.00 g, 27.2 mmol), sulfur (2.03 g, 63.3 mmol) and $Br_2$ (0.96 mL, 18.6 mmol) were heated in an evacuated sealed quartz ampoule at 300° C. for 48 h, after which, the mixture was thoroughly shaken and then heated for another 72 h. Then the ampoule was opened, the solid washed with dichloromethane and hot toluene and dried under vacuum. Yield: 8.9 g (90%) first attempt, 8.5 g (86%) second attempt.

Preparation of $(PPh_4)_2W_3S_7Br_6$ $W_3S_7Br_4$ (17.4 g) was melted together with PPh$_4$Br (35 g) at 300° C. under argon. The cold melt was washed with ethanol to remove PPh$_4$Br, the solid was extracted with hot acetonitrile, and the solution filtered. Addition of ether to the filtrate produced 25.2 g (82%) $(PPh_4)W_3S_7Br_6$.

Preparation of $W_3S_7(coco_2dtc)_4$ $(PPh_4)W_3S_7Br_6$ (12.6 g, 6.5 mmol) and K(coco$_2$dtc) (20 g, 40 mmol) were combined in a flask under argon. The flask was charged with methanol (200 mL) and acetonitrile (100 mL) and heated at 60° C. for 8 h. The solution was decanted and the product was washed three times with hot methanol. The product was dissolved in ether and filtered. The filtrate was removed under vacuum and the product was redissolved in hexane and filtered. After removal of hexane under vacuum 13.8 g or $W_3S_7(dtc)_4$ was recovered.

Example 2

Preparation of $W_3S_4(coco_2dtc)_4$ $(PPh_4)W_3S_7Br_6$ (12.6 g, 6.5 mmol), prepared as in Example 1, and K(coco$_2$dtc) (20 g, 40 mmol) were combined in a flask under argon. The flask was charged with methanol (200 mL) and acetonitrile (100 mL) and heated to 60° C. After 30 minutes, PPh$_3$ (5.1 g, 19.5 mmol) was added to the solution; heating was continued for an additional 7.5 h. The solution was decanted and the product was washed three times with hot methanol. The product was dissolved in ether and filtered. The filtrate was removed under vacuum and the product was redissolved in hexane and filtered. After removal of hexane under vacuum 14.3 g of $W_3S_4dtc_4$ was recovered.

Tests

The tungsten compounds prepared in Examples 1 and 2 above were subjected to the following two tests:
  a PSA (Peugeot S.A.) four-ball test in which a system of balls is fastened in a holder filled with a test oil and subjected to a test load whilst a rotating ball is pressed onto three stationary balls of the same size and quality. Wear is measured as a function of the test load by measuring the average wear scar diameter in mm.
  a differential scanning calorimity (DSC) test in which a sample of test oil, based on Solvent 150 Neutral, is heated at a rate of e.g. 5° C./minute and the rise in sample temperature relative to an inert reference is measured. The temperature at which an exothermic reaction occurs or the oxidation onset temperature is a measure of oxidative stability of the sample. It is believed that higher DSC temperatures indicate improved oxidative stability.

The above tests were carried out on samples of the base case (base oil) and on samples of the base case containing each of the final products of Examples 1 and 2 at a concentration of 150 ppm by mass, expressed as atoms of tungsten, per mass of base oil.

The results were as follows:

|  | | SAMPLE | |
| --- | --- | --- | --- |
| TEST | BASE CASE | WITH EX 1 | WITH EX 2 |
| PSA 4-BALL (mm) | 0.475 | 0.34 | 0.34 |
| DSC (° C.) | 177.8 | 178.2 | 183.4 |

The results show that the tungsten compounds used in the present invention improve both wear and oxidative stability in lubricating oil compositions.

What is claimed is:

1. A lubricating oil composition comprising, or made by mixing, a major amount of an oil of lubricating viscosity and a minor amount of, as an additive, at least one compound comprising a trinuclear tungsten core and bonded thereto a ligand or ligands capable of rendering the compound oil-soluble or oil-dispersible.

2. The composition of claim 1 wherein the core contains non-metallic atoms consisting wholly or partly of sulfur.

3. The composition of claim 1 wherein the core consists of trinuclear tungsten and sulfur.

4. The composition of claim 1 wherein the compound has the formula $W_3S_kL_n$ or mixtures thereof, wherein L represents a ligand which is independent from other ligands represented by L when n is more than 1;

n is in the range from 1 to 4; and k is at least 4.

5. The composition of claim 1 wherein the compound has the formula $W_3S_kE_xL_n$ or mixtures thereof, wherein L represents a ligand which is independent from other ligands represented by L when n is more than 1;

n is in the range from 1 to 4;

k is at least 1, E is oxygen or selenium, x is at least 1, and the sum of k and x is at least 4.

6. The composition of claim 4 wherein the formula additionally includes a moiety $Q_z$, wherein Q represents a neutral electron-donating compound, and z is in the range from 0 to 5.

7. The composition of claim 1, wherein the ligand or ligands, including L, are represented by one or more of the following formulae:

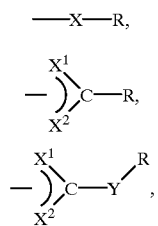

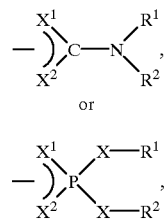

and mixtures thereof, and perthio derivatives thereof, wherein X, $X^1$, $X^2$ and Y are independently selected from the group of oxygen and sulfur, and wherein $R^1$, $R^2$, and R are independently selected from the group consisting of H and organo groups that may be the same or different.

8. The composition of claim 7 wherein the organo groups independently represent alkyl, substituted or unsubstituted aryl, or ether groups.

9. The composition of claim 8 wherein the groups are alkyl groups each having from 1 to 100 carbon atoms.

10. The composition of claim 1, wherein the ligand or ligands are or L independently represents a dialkyldithiophosphate, thioxanthate, dialkylphosphate, dialkyldithiocarbamate, xanthate, or carboxylate ligand.

11. The composition of claim 1, wherein the mass of tungsten from the trinuclear tungsten compound is at least 1 ppm based on the mass of the composition.

12. The composition of claim 1, wherein the total number of carbon atoms in all of the ligands' or all L's organo groups is at least 21.

13. The composition of claim 1, wherein the oil of lubricating viscosity is free of sulphur.

14. The composition of claim 1, further comprising, or made by mixing, at least one antioxidant additive.

15. The composition of claim 14 wherein the antioxidant is a copper-containing antioxidant is a sulfur-containing antioxidant, a phenolic antioxidant, an aromatic amine-containing antioxidant or mixtures thereof.

16. The composition of claim 1, further comprising one or more dispersants, detergents, pour point depressants, viscosity modifiers, surfactants and antiwear agents.

17. An additive concentrate for blending with an oil of lubricating viscosity comprising, or made by mixing, an oleaginous carrier and from 1 to 200,000 ppm by mass of the tungsten of a compound as defined in claim 1, based on the mass of the concentrate.

18. An additive concentrate of claim 17 further comprising, or made by mixing, at least one antioxidant additive selected from a copper-containing antioxidant, a sulfur-containing antioxidant, a phenolic antioxidant, an aromatic amine-containing antioxidant amd mixtures thereof, whereby the concentrate contains from 1 to 90 mass % of additives based on the mass of the concentrate.

19. A compound having the formula $W_3S_kL_nQ_Z$ wherein L represents a ligand or independently selected ligands, n is from 1 to 4, k is at least 4, Q is a neutral electron donating compound, and z ranges from 0 to 5, wherein the compound has a core having the structure

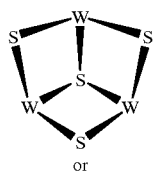

(I)

or

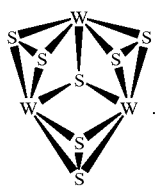

(II)

20. A method of lubricating an internal combustion engine comprising operating the engine and lubricating the engine with a lubricating oil composition as claimed in claim 1.

21. A method for preparing a compound comprising a trinuclear thiotungsten core and bonded thereto a ligand or ligands capable of rendering the compound oil-soluble or oil-dispersible, which method comprises reacting a trinuclear thiotungsten source and a source of said ligand or ligands to form said compound.

22. The method of claim 21 wherein the tungsten source is a compound containing the $[W_3S_4 \text{ or }_7X_6]^{2-}$ ion where X represents halogen such as chlorine or bromine.

23. The composition of claim 5 wherein the formula additionally includes a moiety $Q_z$, wherein Q represents a neutral electron-donating compound, and z is in the range from 0 to 5.

24. A method of enhancing one or more lubricating properties of an oil of lubricating viscosity comprising adding to said oil an additive comprising at least one compound comprising a trinuclear tungsten core having bonded thereto a ligand or ligands capable of rendering the compound oil-soluble or oil-dispersible.

* * * * *